United States Patent
Rose et al.

(10) Patent No.: US 6,441,044 B1
(45) Date of Patent: Aug. 27, 2002

(54) CYCLOALKYL CARBOXYLIC ACID AMIDES, THEIR PRODUCTION AND THEIR USE AS FUNGICIDES IN AGRICULTURE

(75) Inventors: Ingo Rose, Mannheim; Frank Wetterich; Karl Eicken, both of Wachenheim; Joachim Rheinheimer, Ludwigshafen; Gisela Lorenz, Neustadt; Eberhard Ammermann, Heppenheim; Thomas Grote, Schifferstadt; Siegfried Strathmann, Limburgerhof, all of (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/763,685

(22) PCT Filed: Aug. 26, 1999

(86) PCT No.: PCT/EP99/06251

§ 371 (c)(1),
(2), (4) Date: Feb. 26, 2001

(87) PCT Pub. No.: WO00/12465

PCT Pub. Date: Mar. 9, 2000

(30) Foreign Application Priority Data

Sep. 1, 1998 (DE) .......................... 198 39 690

(51) Int. Cl.⁷ ...................... A01N 37/18; A61K 31/165; C07C 233/57; C07C 235/40
(52) U.S. Cl. ........................................ 514/624; 564/190
(58) Field of Search ............................ 564/190; 514/624

(56) References Cited

U.S. PATENT DOCUMENTS

| | | | |
|---|---|---|---|
| 4,710,518 A | * 12/1987 | Kurahashi et al. | .......... 514/624 |
| 4,988,734 A | 1/1991 | Kraatz | |
| 5,061,731 A | 10/1991 | Kurahashi et al. | |

FOREIGN PATENT DOCUMENTS

| | | |
|---|---|---|
| EP | 170 842 | 12/1986 |
| EP | 257 448 | 3/1988 |
| EP | 341 475 | 11/1989 |
| WO | 97/35838 | 10/1997 |
| WO | 98/41499 | 9/1998 |
| WO | 99/31048 | 6/1999 |

OTHER PUBLICATIONS

J.Chro.,585(1991) 195–206, Straub et al.
Chirality,vol. 9, 497–423 (1997) Kuball et al.

* cited by examiner

Primary Examiner—Brian J. Davis
(74) Attorney, Agent, or Firm—Keil & Weinkauf

(57) ABSTRACT

The present invention relates to cycloalkylcarboxamides of formula I

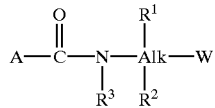

where:
  A is optionally substituted $C_3$–$C_6$-cycloalkyl;
  Alk is straight-chain or branched $C_1$–$C_6$-alkylene;
  $R^1$ is optionally substituted $C_1$–$C_6$-alkyl or $C_2$–$C_6$-alkenyl;
  $R^2$, $R^3$ is hydrogen, or is optionally halogenated $C_1$–$C_6$-alkyl or $C_2$–$C_6$-alkenyl;
  W is an optionally substituted fused bicyclic ring system having in each case six ring atoms, where one or two carbon ring atoms may be replaced by nitrogen atoms;
and their agriculturally useful salts.

Furthermore, the invention relates to fungicidal compositions comprising a compound of formula I as crop protection agent.

11 Claims, No Drawings

CYCLOALKYL CARBOXYLIC ACID AMIDES, THEIR PRODUCTION AND THEIR USE AS FUNGICIDES IN AGRICULTURE

The present invention relates to novel cycloalkylcarboxamides of the formula I

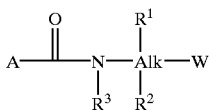

where:
- A is $C_3$–$C_6$-cycloalkyl which may carry one or more substituents selected from the group consisting of halogen, cyano, $C_1$–$C_6$-alkyl, $C_2$–$C_6$-alkenyl, $C_1$–$C_6$-alkoxy or $C_1$–$C_6$-alkylthio;
- Alk is straight-chain or branched $C_1$–$C_6$-alkylene;
- $R^1$ is $C_1$–$C_6$-alkyl or $C_2$–$C_6$-alkenyl, where these radicals may be partially or fully halogenated and/or may carry one or two of the following groups: $C_1$–$C_4$-alkoxy, $C_1$–$C_4$-haloalkoxy, $C_1$–$C_4$-alkylthio, $C_1$–$C_4$-alkoxycarbonyl, $C_3$–$C_6$-cycloalkyl and phenyl, where the phenyl may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_3$–$C_6$-cycloalkyl or heterocyclyl;
- $R^2$, $R^3$ are hydrogen, $C_1$–$C_6$-alkyl or $C_2$–$C_6$-alkenyl, where these radicals may be partially or fully halogenated;
- W is a fused bicyclic ring system having in each case six ring atoms, where one or two carbon ring atoms may be replaced by nitrogen atoms, and where these ring systems may carry one to three of the following groups: nitro, halogen, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_3$–$C_6$-cycloalkyl and $C_1$–$C_4$-alkoxycarbonyl;

and their agriculturally useful salts.

EP 0 170 842 describes N-benzylcyclopropanecarboxamide derivatives and their use as fungicides in agriculture. The compounds described therein are cyclopropylcarboxamides which carry a phenylalkyl group in the amide moiety and which are substituted in the 2-position of the cyclopropane ring by two chlorine atoms. U.S. Pat. No. 4,988,734 describes the corresponding N-(R)-(1-phenylethyl)-1-alkyl-2,2-dichlorocyclopropanecarboxamide stereoisomers. Furthermore, U.S. Pat. No. 5,034,408 describes further 2,2-dichlorocyclopropanecarboxamides which contain a second carboxamide group in the carboxamide moiety. Furthermore, PCT/EP98/01031 discloses α-halo- and α-cyanosubstituted carboxamides having fungicidal action.

The fungicidal properties of the known compounds are, with respect to their activity against harmful fungi such as, for example, *Pyricularia oryzae* not always entirely satisfactory.

It is an object of the present invention to provide novel carboxamides which are active against harmful fungi.

We have found that this object is achieved by the cycloalkylcarboxamides I defined at the outset. Furthermore, we have found processes for preparing the compounds I and the intermediates of the formula II which are required for their preparation. We have found compositions comprising the compounds I, methods for controlling harmful fungi using the compounds I and, finally, the use of the compounds I for controlling harmful fungi.

Depending on the substitution pattern, the compounds of the formula I may contain one or more chiral centers. In this case, they are present as mixtures of enantiomers or diastereomers. The invention provides both the pure enantiomers or diastereomers and their mixtures.

In the definition of the compounds I given at the outset, collective terms were used for the radicals $R^1$ to $R^3$ and A which represent individual enumerations of the specific group members. In each of the abovementioned cases, the radicals alkyl, alkylthio, alkoxy, alkoxycarbonyl and alkenyl may be straight-chain or branched.

The term "partially or fully halogenated" is meant to express that the hydrogen atoms in the groups characterized in this way may be partly or fully replaced by identical or different halogen atoms. In each case, the term "halogen" represents fluorine, chlorine, bromine or iodine.

In the case where W is a naphthyl ring in which one or two carbon ring atoms are replaced by nitrogen atoms, it is to be understood as a quinoline, isoquinoline or naphthyridine system.

Examples of other meanings for each of the abovementioned cases are:

$C_1$–$C_4$-alkyl, and the alkyl moieties of $C_1$–$C_4$-alkylthio:
  methyl, ethyl, propyl, 1-methylethyl, butyl, 1-methylpropyl, 2-methylpropyl and 1,1-dimethylethyl;

$C_1$–$C_6$-alkyl:
  $C_1$–$C_6$-alkyl as mentioned above, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_4$-haloalkyl:
  a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_4$-alkoxy, and the alkoxy moieties of $C_1$–$C_4$-alkoxycarbonyl:
  methoxy, ethoxy, propoxy, 1-methylethoxy, butoxy, 1-methylpropoxy, 2-methylpropoxy and 1,1-dimethylethoxy;

$C_1$–$C_4$-haloalkoxy: a $C_1$–$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_2$–$C_6$-alkenyl: ethylene, prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl and 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

$C_3$–$C_6$-cycloalkyl: cyclopropyl, cyclobutyl, cyclopentyl, cyclohexyl; preferably cyclopropyl;

$C_1$–$C_6$-alkylene: a straight-chain or branched alkylene group having 1–6 carbon atoms, such as, for example, methylene, 1,1-ethylene, 1,2-ethylene, 1,1-propylene, 1,2-propylene, 1,3-propylene, 1,1-butylene, 1,2-butylene, 1,3-butylene, 1,4-butylene; in particular methylene.

$C_1$–$C_6$-alkyl or $C_2$–$C_6$-alkenyl, where these radicals may be partially or fully halogenated: the corresponding radicals which have been mentioned under $C_1$–$C_6$-haloalkyl, where, in the case of the alkenyl radicals, the radicals mentioned beforehand in the definition of alkenyl are suitable.

In the context of the present invention, preference is given to cycloalkylcarboxamides I having the following substituents, where the preference is valid both on its own or in combination with the other definitions:

$R^1$ is preferably $C_1$–$C_6$-alkyl, such as, for example, methyl or ethyl. $R^2$ is preferably hydrogen or $C_1$–$C_6$-alkyl, such as, for example, methyl or ethyl. Particular preference is given to compounds I where $R^1$ is methyl and $R^2$ is hydrogen.

W is preferably 1-naphthyl or 2-naphthyl.

Alk is preferably the methylene group, giving compounds of the type —C($R^3$)($R^4$)—.

In the formula I, A is preferably a cyclopropyl ring, giving compounds of the formula Ia:

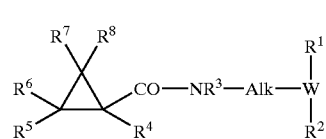

where the substituents $R^4$–$R^8$ are as defined below:

$^4$ is hydrogen, halogen, cyano, $C_1$–$C_6$-alkyl, $C_2$–$C_6$-alkenyl, $C_1$–$C_6$-alkoxy or $C_1$–$C_6$-alkylthio, where these radicals may be partially or fully halogenated and/or may carry one or two of the following groups: $C_1$–$C_4$-alkoxy, $C_1$–$C_4$-haloalkoxy, $C_1$–$C_4$-alkylthio, $C_1$–$C_4$-alkoxycarbonyl, $C_3$–$C_6$-cycloalkyl, $C_1$–$C_4$-alkoxycarbonylamino;

$^5$ is hydrogen, halogen, cyano, $C_1$–$C_6$-alkyl, $C_2$–$C_6$-alkenyl, $C_1$–$C_6$-alkoxy or $C_1$–$C_6$-alkylthio, where these radicals may be partially or fully halogenated and/or may carry one or two of the following groups: $C_1$–$C_4$-alkoxy, $C_1$–$C_4$-haloalkoxy, $C_1$–$C_4$-alkylthio, $C_1$–$C_4$-alkoxycarbonyl, $C_3$–$C_6$-cycloalkyl, $C_1$–$C_4$-alkoxycarbonylamino;

$^6$ is hydrogen, halogen or $C_1$–$C_6$-alkyl;

$^7$ is hydrogen, halogen or $C_1$–$C_6$-alkyl;

$^8$ is hydrogen, halogen or $C_1$–$C_6$-alkyl.

In the formula Ia, the radicals $R^4$–$R^8$ have in particular the following meanings, in each case on their own or in combination with each other:

a. Compounds of the formula Ia where $R^4$ is hydrogen, halogen, cyano, $C_1$–$C_6$-alkyl, $C_1$–$C_4$-alkoxycarbonylamino; such as, for example, methyl, ethyl, methoxycarbonylamino, ethoxycarbonylamino or isopropyloxycarbonylamino.

b. Compounds of the formula Ia where $R^5$ is hydrogen, $C_1$–$C_6$-alkyl; such as, for example, methyl or ethyl.

c. Compounds of the formula Ia where $R^6$ is hydrogen, $C_1$–$C_6$-alkyl; such as, for example, methyl or ethyl; preferably hydrogen.

d. Compounds of the formula Ia where $R^7$ is hydrogen, chlorine or $C_1$–$C_6$-alkyl, such as, for example, methyl.

e. Compounds of the formula Ia where $R^8$ is hydrogen, chlorine or $C_1$–$C_6$-alkyl; such as, for example, methyl.

With respect to $R^4$–$R^8$, the cyclopropyl ring may be mono- to pentasubstituted.

Monosubstituted cyclopropyl derivatives of the formula Ia are those compounds where a total of four of the radicals $R^4$–$R^8$ are hydrogen. Examples include those compounds where $R^4$ is alkyl, halogen, cyano or alkoxycarbonylamino.

Disubstituted cyclopropyl derivatives of the formula Ia are those compounds where a total of three of the radicals $R^4$–$R^8$ are hydrogen. Examples include those compounds where $R^4$ is $C_1$–$C_6$-alkyl, halogen or cyano and $R^5$ is $C_1$–$C_6$-alkyl. Preferred disubstituted cyclopropyl derivatives are furthermore those compounds in which $R^7$ and $R^8$ are halogen or $C_1$–$C_6$-alkyl.

Trisubstituted cyclopropyl derivatives of the formula Ia are those compounds where a total of two of the radicals $R^4$–$R^8$ are hydrogen. Examples include compounds where: $R^4$=$C_1$–$C_6$-alkyl, halogen or cyano; $R^7$=halogen or $C_1$–$C_6$-alkyl; $R^8$=halogen or $C_1$–$C_6$-alkyl.

Tetrasubstituted cyclopropyl derivatives of the formula Ia are compounds in which one of the radicals $R^4$–$R^8$ is hydrogen. Examples include those compounds where $R^5$ or $R^6$ is hydrogen. The other substituents have, for example, the following meanings: $R^4$=$C_1$–$C_6$-alkyl, halogen or cyano; $R^6$=$C_1$–$C_6$-alkyl; $R^7$=halogen or $C_1$–$C_6$-alkyl; $R^8$=halogen or $C_1$–$C_6$-alkyl.

Pentasubstituted cyclopropyl derivatives of the formula Ia are compounds in which none of the radicals $R^4$–$R^8$ are hydrogen. Examples include those compounds where $R^4$ is $C_1$–$C_6$-alkyl, halogen or cyano and $R^5$–$R^8$ are $C_1$–$C_6$-alkyl.

Independently of the abovementioned substitution patterns, preference is given to those compounds of the formula Ia in which $R^7$ and $R^8$ are identical and are each halogen, in particular chlorine, or $C_1$–$C_6$-alkyl, in particular methyl.

If the alkylene chain Alk contains a chiral carbon, this is preferably in the R configuration.

If the compounds of the formula Ia have one or more centers of asymmetry, both the stereoisomeric mixtures and the corresponding enantiomers or diastereomers are suitable in the context of the present invention. With regard to the stereochemical arrangement of the substituents $R^4$ and $R^5$, preference is given to the compounds of the formula Ib:

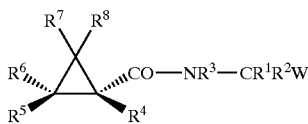

Ib

With a view to their use, particular preference is given to the compounds Ia compiled in Tables 1 and 2 below.

Table 1

Carboxamides Ic.001 to Ic.144 of the formula Ic where W is a naphthyl group and $R^7$ and $R^8$ are each a methyl group. If $R^1$ and $R^2$ are different, compounds can be present either as racemic mixtures or in the form of their enantiomers, or of mixtures thereof. Here, the carbon labeled with "*" can either have the R configuration or the S configuration. Preference is given to the R configuration.

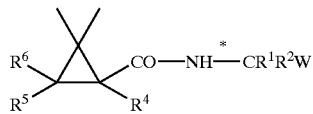

Ic

| No. | $R^1$ | $R^2$ | $R^4$ | $R^5$ | $R^6$ |
|---|---|---|---|---|---|
| Ic.001 | H | H | H | H | H |
| Ic.002 | H | $CH_3$ | H | H | H |
| Ic.003 | $CH_3$ | $CH_3$ | H | H | H |
| Ic.004 | H | H | CN | H | H |
| Ic.005 | H | $CH_3$ | CN | H | H |
| Ic.006 | $CH_3$ | $CH_3$ | CN | H | H |
| Ic.007 | H | H | $CH_3$ | H | H |
| Ic.008 | H | $CH_3$ | $CH_3$ | H | H |
| Ic.009 | $CH_3$ | $CH_3$ | $CH_3$ | H | H |
| Ic.010 | H | H | $C_2H_5$ | H | H |
| Ic.011 | H | $CH_3$ | $C_2H_5$ | H | H |
| Ic.012 | $CH_3$ | $CH_3$ | $C_2H_5$ | H | H |
| Ic.013 | H | H | $SCH_3$ | H | H |
| Ic.014 | H | $CH_3$ | $SCH_3$ | H | H |
| Ic.015 | $CH_3$ | $CH_3$ | $SCH_3$ | H | H |
| Ic.016 | H | H | $OCH_3$ | H | H |
| Ic.017 | H | $CH_3$ | $OCH_3$ | H | H |
| Ic.018 | $CH_3$ | $CH_3$ | $OCH_3$ | H | H |
| Ic.019 | H | H | F | H | H |
| Ic.020 | H | $CH_3$ | F | H | H |
| Ic.021 | $CH_3$ | $CH_3$ | F | H | H |
| Ic.022 | H | H | Cl | H | H |
| Ic.023 | H | $CH_3$ | Cl | H | H |
| Ic.024 | $CH_3$ | $CH_3$ | Cl | H | H |
| Ic.025 | H | H | Br | H | H |
| Ic.026 | H | $CH_3$ | Br | H | H |
| Ic.027 | $CH_3$ | $CH_3$ | Br | H | H |
| Ic.028 | H | H | I | H | H |
| Ic.029 | H | $CH_3$ | I | H | H |
| Ic.030 | $CH_3$ | $CH_3$ | I | H | H |
| Ic.031 | H | H | H | $CH_3$ | H |
| Ic.032 | H | $CH_3$ | H | $CH_3$ | H |
| Ic.033 | $CH_3$ | $CH_3$ | H | $CH_3$ | H |
| Ic.034 | H | H | CN | $CH_3$ | H |
| Ic.035 | H | $CH_3$ | CN | $CH_3$ | H |
| Ic.036 | $CH_3$ | $CH_3$ | CN | $CH_3$ | H |
| Ic.037 | H | H | H | $C_2H_5$ | H |
| Ic.038 | H | $CH_3$ | H | $C_2H_5$ | H |
| Ic.039 | $CH_3$ | $CH_3$ | H | $C_2H_5$ | H |
| Ic.040 | H | H | CN | $C_2H_5$ | H |
| Ic.041 | H | $CH_3$ | CN | $C_2H_5$ | H |
| Ic.042 | $CH_3$ | $CH_3$ | CN | $C_2H_5$ | H |
| Ic.043 | H | H | H | $SCH_3$ | H |
| Ic.044 | H | $CH_3$ | H | $SCH_3$ | H |
| Ic.045 | $CH_3$ | $CH_3$ | H | $SCH_3$ | H |
| Ic.046 | H | H | CN | $SCH_3$ | H |
| Ic.047 | H | $CH_3$ | CN | $SCH_3$ | H |
| Ic.048 | $CH_3$ | $CH_3$ | CN | $SCH_3$ | H |
| Ic.049 | H | H | H | $OCH_3$ | H |
| Ic.050 | H | $CH_3$ | H | $OCH_3$ | H |
| Ic.051 | $CH_3$ | $CH_3$ | H | $OCH_3$ | H |
| Ic.052 | H | H | CN | $OCH_3$ | H |
| Ic.053 | H | $CH_3$ | CN | $OCH_3$ | H |
| Ic.054 | $CH_3$ | $CH_3$ | CN | $OCH_3$ | H |
| Ic.055 | H | H | H | F | H |
| Ic.056 | H | $CH_3$ | H | F | H |
| Ic.057 | $CH_3$ | $CH_3$ | H | F | H |
| Ic.058 | H | H | CN | F | H |
| Ic.059 | H | $CH_3$ | CN | F | H |
| Ic.060 | $CH_3$ | $CH_3$ | CN | F | H |
| Ic.061 | H | H | H | Cl | H |
| Ic.062 | H | $CH_3$ | H | Cl | H |
| Ic.063 | $CH_3$ | $CH_3$ | H | Cl | H |
| Ic.064 | H | H | CN | Cl | H |
| Ic.065 | H | $CH_3$ | CN | Cl | H |
| Ic.066 | $CH_3$ | $CH_3$ | CN | Cl | H |
| Ic.067 | H | H | H | Br | H |
| Ic.068 | H | $CH_3$ | H | Br | H |
| Ic.069 | $CH_3$ | $CH_3$ | H | Br | H |
| Ic.070 | H | H | CN | Br | H |
| Ic.071 | H | $CH_3$ | CN | Br | H |
| Ic.072 | $CH_3$ | $CH_3$ | CN | Br | H |
| Ic.073 | H | H | H | H | $CH_3$ |
| Ic.074 | H | $CH_3$ | H | H | $CH_3$ |
| Ic.075 | $CH_3$ | $CH_3$ | H | H | $CH_3$ |
| Ic.076 | H | H | CN | H | $CH_3$ |
| Ic.077 | H | $CH_3$ | CN | H | $CH_3$ |

-continued

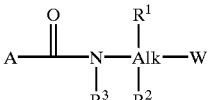

Ic

| No. | R¹ | R² | R⁴ | R⁵ | R⁶ |
|---|---|---|---|---|---|
| Ic.078 | CH₃ | CH₃ | CN | H | CH₃ |
| Ic.079 | H | H | CH₃ | H | CH₃ |
| Ic.080 | H | CH₃ | CH₃ | H | CH₃ |
| Ic.081 | CH₃ | CH₃ | CH₃ | H | CH₃ |
| Ic.082 | H | H | C₂H₅ | H | CH₃ |
| Ic.083 | H | CH₃ | C₂H₅ | H | CH₃ |
| Ic.084 | CH₃ | CH₃ | C₂H₅ | H | CH₃ |
| Ic.085 | H | H | SCH₃ | H | CH₃ |
| Ic.086 | H | CH₃ | SCH₃ | H | CH₃ |
| Ic.087 | CH₃ | CH₃ | SCH₃ | H | CH₃ |
| Ic.088 | H | H | OCH₃ | H | CH₃ |
| Ic.089 | H | CH₃ | OCH₃ | H | CH₃ |
| Ic.090 | CH₃ | CH₃ | OCH₃ | H | CH₃ |
| Ic.091 | H | H | F | H | CH₃ |
| Ic.092 | H | CH₃ | F | H | CH₃ |
| Ic.093 | CH₃ | CH₃ | F | H | CH₃ |
| Ic.094 | H | H | Cl | H | CH₃ |
| Ic.095 | H | CH₃ | Cl | H | CH₃ |
| Ic.096 | CH₃ | CH₃ | Cl | H | CH₃ |
| Ic.097 | H | H | Br | H | CH₃ |
| Ic.098 | H | CH₃ | Br | H | CH₃ |
| Ic.099 | CH₃ | CH₃ | Br | H | CH₃ |
| Ic.100 | H | H | I | H | CH₃ |
| Ic.101 | H | CH₃ | I | H | CH₃ |
| Ic.102 | CH₃ | CH₃ | I | H | CH₃ |
| Ic.103 | H | H | H | CH₃ | CH₃ |
| Ic.104 | H | CH₃ | H | CH₃ | CH₃ |
| Ic.105 | CH₃ | CH₃ | H | CH₃ | CH₃ |
| Ic.106 | H | H | CN | CH₃ | CH₃ |
| Ic.107 | H | CH₃ | CN | CH₃ | CH₃ |
| Ic.108 | CH₃ | CH₃ | CN | CH₃ | CH₃ |
| Ic.109 | H | H | H | C₂H₅ | CH₃ |
| Ic.110 | H | CH₃ | H | C₂H₅ | CH₃ |
| Ic.111 | CH₃ | CH₃ | H | C₂H₅ | CH₃ |
| Ic.112 | H | H | CN | C₂H₅ | CH₃ |
| Ic.113 | H | CH₃ | CN | C₂H₅ | CH₃ |
| Ic.114 | CH₃ | CH₃ | CN | C₂H₅ | CH₃ |
| Ic.115 | H | H | H | SCH₃ | CH₃ |
| Ic.116 | H | CH₃ | H | SCH₃ | CH₃ |
| Ic.117 | CH₃ | CH₃ | H | SCH₃ | CH₃ |
| Ic.118 | H | H | CN | SCH₃ | CH₃ |
| Ic.119 | H | CH₃ | CN | SCH₃ | CH₃ |
| Ic.120 | CH₃ | CH₃ | CN | SCH₃ | CH₃ |
| Ic.121 | H | H | H | OCH₃ | CH₃ |
| Ic.122 | H | CH₃ | H | OCH₃ | CH₃ |
| Ic.123 | CH₃ | CH₃ | H | OCH₃ | CH₃ |
| Ic.124 | H | H | CN | OCH₃ | CH₃ |
| Ic.125 | H | CH₃ | CN | OCH₃ | CH₃ |
| Ic.126 | CH₃ | CH₃ | CN | OCH₃ | CH₃ |
| Ic.127 | H | H | H | F | CH₃ |
| Ic.128 | H | CH₃ | H | F | CH₃ |
| Ic.129 | CH₃ | CH₃ | H | F | CH₃ |
| Ic.130 | H | H | CN | F | CH₃ |
| Ic.131 | H | CH₃ | CN | F | CH₃ |
| Ic.132 | CH₃ | CH₃ | CN | F | CH₃ |
| Ic.133 | H | H | H | Cl | CH₃ |
| Ic.134 | H | CH₃ | H | Cl | CH₃ |
| Ic.135 | CH₃ | CH₃ | H | Cl | CH₃ |
| Ic.136 | H | H | CN | Cl | CH₃ |
| Ic.137 | H | CH₃ | CN | Cl | CH₃ |
| Ic.138 | CH₃ | CH₃ | CN | Cl | CH₃ |
| Ic.139 | H | H | H | Br | CH₃ |
| Ic.140 | H | CH₃ | H | Br | CH₃ |
| Ic.141 | CH₃ | CH₃ | H | Br | CH₃ |
| Ic.142 | H | H | CN | Br | CH₃ |
| Ic.143 | H | CH₃ | CN | Br | CH₃ |
| Ic.144 | CH₃ | CH₃ | CN | Br | CH₃ |

Carboxamides Id.001 to Id.144 of the formula Id in which the meanings of the combinations of $R^1$–$R^6$ are given by the rows of Table 1, W is naphthyl and $R^7$ and $R^8$ are chlorine.

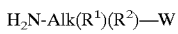

Id

According to a process which is preferred according to the invention, the carboxamides I

I $$A\overset{O}{\underset{R^3}{\|}}\!\!-\!\!N\!\!-\!\!\underset{R^2}{Alk}\!\!-\!\!W$$

are obtained by reacting the carboxylic acid derivatives II, $$A\!-\!CO\!-\!X \qquad \qquad II$$

with amines of the formula III $$H_2N\text{-}Alk(R^1)(R^2)\!-\!W \qquad \qquad III$$

where X is a group that is readily cleavable.

The amide formation is carried out according to processes known from the literature. The free carboxylic acids of the formula II' where X is hydroxyl are generally first converted into an activated carboxylic acid derivative II where X is, for example, chlorine.

The activation of the carboxylic acids II' can preferably also be carried out in situ by using the carboxylic acids II' directly with addition of, for example, dicyclohexylcarbodiimide, ethyl chloroformate, diethyl cyanophosphonate, triphenylphosphine/azodicarboxylic ester, 2-pyridine disulfide/triphenylphosphine, carbonyldiimidazole, thionyl chloride, phosphorus trichloride, phosphorus pentachloride, etc. The carbodiimides, for example, are generally added in equimolar amounts, based on the carboxylic acids II'.

The activation of the carboxylic acids via acyl cyanides is carried out for example by reacting the carboxylic acids II' with diethyl cyanophosphonates, preferably in an inert solvent such as tetrahydrofuran, toluene or dichloromethane (cf. Tetrahedron Lett. 18 (1973), 1595–8).

The activation via anhydrides is carried out, for example, by reacting the carboxylic acids II' with chloroformates, such as ethyl chloroformate, generally in the presence of bases, and, if appropriate, in an inert solvent, such as toluene or tetrahydrofuran (cf. "Houben-Weyl", 4th edition (1974), 15/1, pages 28–32).

The amide formation is preferably carried out in the presence of bases, such as tertiary amines, for example, triethylamine or dimethylcyclohexylamine, alkali metal carbonates, alkali metal hydroxides, pyridine etc. The starting materials and the auxiliary base are advantageously employed in equimolar amounts. In certain cases, a slight excess of auxiliary base of 0.1–0.5 equivalents may be helpful.

Suitable solvents are aliphatic hydrocarbons, such as hexane and ligroin, aromatic hydrocarbons, such as toluene and xylene, chlorinated hydrocarbons, such as methylene chloride and 1,2-dichloroethane, ethers, such as methyl tert-butyl ether and tetrahydrofuran, polar aprotic solvents, such as acetonitrile and dimethylformamide, or esters, such as ethyl acetate, or mixtures of these.

The molar ratio of carboxylic acid derivatives II to amine III is generally from 0.8 to 1.5 and preferably from 0.9 to 1.1.

After the reaction has gone to completion, the reaction mixture is subjected to customary work-up, for example by introducing it into water and subsequently extracting the amide using an organic solvent.

The carboxylic acids of the formula II are known, or they can be prepared by similar methods known from the literature. In the case where A is a cyclopropyl radical, the carboxylic acids can be prepared in accordance with the following scheme:

Scheme 1

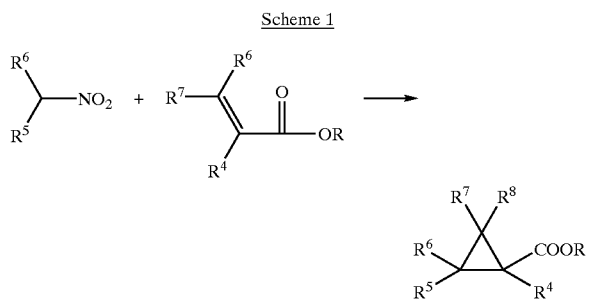

The amines of the formula III are known, or they can be obtained by methods known from the literature (cf. Organikum (1993) Barth Verlagsgesellschaft mbH Leipzig, p. 509 ff; "Houben-Weyl", Vol. 15/1, pp. 648–665); Indian J. Chem. 10 (1972) 366).

The R isomer can be separated off from racemates of the amines III in a manner known per se, for example by fractional crystallization using optically active tartaric acid or, preferably, by enzyme-catalyzed esterification and subsequent hydrolysis (cf., for example, WO 95/08636).

The condensation is usually carried out in a water-immiscible solvent such as hexane, toluene or xylene, and the water formed during the reaction is removed. To this end, the reaction mixture is heated at the boil under reflux for a number of hours.

Suitable-catalysts are bases, such as, for example, piperidine, pyridine, ammonia or β-alanine in the presence of an acid, such as, for example, glacial acetic acid.

X is a nucleophilically replaceable radical, such as hydroxyl, $C_1$–$C_4$-alkoxy, halogen for example bromine or chlorine, hetaryl, for example imidazolyl or pyridyl, carboxylate, for example acetate or trifluoroacetate, etc.

Particular preference is given to carboxylic acid derivatives of the formula II in which A is unsubstituted or substituted cyclopropyl.

The compounds I have excellent activity against a broad spectrum of phytopathogenic fungi, in particular from the classes of the Ascomycetes, Deuteromycetes, Phycomycetes and Basidiomycetes. Some of them act systemically and can be employed in crop protection as foliar- and soil-acting fungicides.

They are especially important for controlling a large number of fungi in a variety of crop plants such as wheat, rye, barley, oats, rice, maize, grass, bananas, cotton, soya, coffee, sugar cane, grape vines, fruit species, ornamentals and vegetable species such as cucumbers, beans, tomatoes, potatoes and cucurbits, and also in the seeds of these plants.

Specifically, they are suitable for controlling the following plant diseases: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grape vines, *Puccinia species* in cereals, Rhizoctonia species in cotton, rice and lawns, Ustilago species in cereals and sugar cane, and *Venturia inaequalis* (scab) in apples, Helminthosporium species in cereals, *Septoria nodorum* in wheat, *Botrytis cinerea* (gray mold) in strawberries, vegetables, ornamentals and grape vines, *Cercospora arachidicola* in groundnuts, *Pseudocercosporella herpotrichoides* in wheat and barley, *Pyricularia oryzae* in rice, *Phytophthora infestans* in potatoes and tomatoes, Fusarium and Verticillium species in a variety of plants, *Plasmopara viticola* in grape vines, Pseudoperonospora species in hops and cucumbers, Alternaria species in vegetables and fruit and Mycosphaerella species in bananas.

The compounds I are also suitable for controlling harmful fungi in the protection of materials (for example wood, paper, paint dispersions, fibers and fabrics) and in the protection of stored products.

The compounds I are employed by treating the fungi or the plants, seeds, materials or the soil to be protected against fungal attack with a fungicidally effective amount of the active compounds. The application is carried out before or after the infection of the materials, plants or seeds by the fungi.

They can be converted into the customary formulations, e.g. solutions, emulsions, suspensions, dusts, powders, pastes and granules. The use form depends on the specific intended use; in any case, it should guarantee fine and uniform distribution of the compound according to the invention. The formulations are prepared in a known manner, e.g. by extending the active compound with solvents and/or carriers, if desired using emulsifiers and dispersants, it being possible to use other organic solvents as auxiliary solvents if water is used as the diluent. Suitable auxiliaries for this purpose are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolin, clays, talc, chalk) and ground synthetic minerals (e.g. finely divided silica, silicates); emulsifiers such as nonionic and anionic emulsifiers (e.g. polyoxyethylene fatty alcohol ethers, alkylsulfonates and arylsulfonates), and dispersants such as lignin-sulfite waste liquors and methylcellulose.

The fungicidal compositions generally comprise from 0.1 to 95, preferably from 0.5 to 90% by weight of active compound.

For use in crop protection, the application rates are, depending on the kind of effect desired, from 0.01 to 2.0 kg of active compound per ha.

The treatment of seeds generally requires active compound quantities of from 0.001 to 0.1 g, preferably from 0.01 to 0.05 g, per kilogram of seed.

For use in the protection of materials or stored products, the active compound application rate depends on the kind of application area and effect desired. Customary application rates in the protection of materials are, for example, from 0.001 g to 2 kg, preferably from 0.005 g to 1 kg, of active compound per cubic meter of treated material.

The compositions according to the invention in the use form as fungicides may also be present in combination with other active compounds, for example with herbicides, insecticides, growth regulators, fungicides or else with fertilizers.

In many cases, this results in a broader fungicidal spectrum of activity.

The following list of fungicides in combination with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide;

nitro derivatives, such as dinitro-(1-methylheptyl)phenyl crotonate, 2-sec-butyl-4,6-dinitrophenyl-3,3-dimethyl acrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(furyl-(2)) benzimidazole, 2-(thiazolyl-(4))benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-mercapto 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis-1-(2,2,2-trichloroethyl) formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methyl-propyl]piperidine, 1-[2-(2,4-dichlorophenyl)-4-ethyl-1,3-di-oxolan-2-ylethyl]-1H-1,2,4-triazole, 1-[2-(2,4-dichloro-phenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS, 3RS)-1-[3-(2-chlorophenyl)-2-(4-fluorophenyl)-oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis-(3-methoxycarbonyl-2-thioureido)benzene, strobilurins, such as methyl E-methoximino-[α-(o-tolyloxy)-o-tolyl]acetate, methyl E-2-{2-[6-(2-cyanophenoxy)-pyridimin-4-yloxy]-phenyl}-3-methoxy-acrylate, N-methyl E-methoximino-[α-(2-phenoxyphenyl)]acetamide, methyl-E-methoximino-[α-(2,5-dimethylphenoxy)-o-tolyl]acetamide, anilinopyrimidines, such as N-(4,6-dimethylpyrimidin-2-yl)aniline, N-[4-methyl-6-(1-propynyl)pyrimidin-2-yl] aniline, N-(4-methyl-6-cyclopropylpyrimidin-2-yl) aniline, phenylpyrroles, such as 4-(2,2-difluoro-1,3-benzodioxol-4-yl)pyrrole-3-carbonitrile, cinnamamides, such as 3-(4-chlorophenyl)-3-(3,4-dimethoxy-phenyl)acryloylmorpholine.

and a variety of fungicides, such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl) alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazol-idine, 3-[3,5-dichlorophenyl-5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis-(4-fluorophenyl) methylsilyl)methyl)-1H-1,2,4-triazole.

The active compounds can be applied as such, in the form of their formulations or in the application forms prepared therefrom, for example in the form of directly sprayable solutions, powders, suspensions or dispersions, emulsions, oil dispersions, pastes, dusts, compositions for broadcasting, or granules, by spraying, atomizing, dusting, broadcasting or watering. The application forms depend entirely on the intended uses; in any case, they should guarantee very fine dispersion of the active compounds according to the invention.

The active compound concentrations in the ready-to-use preparations can be varied over a relatively wide range. In general, they are from 0.0001 to 10%, preferably from 0.01 to 1%.

It is also possible to use the active compounds with good success in the ultra-low-volume method (ULV), it being possible to apply formulations comprising more than 95% by weight of active compound or even the active compound without additives.

For controlling animal pests under free range conditions, the application rate of active compound is from 0.1 to 2.0, preferably 0.2 to 1.0, kg/ha.

Suitable for preparing directly sprayable solutions, emulsions, pastes or oil dispersions are petroleum fractions having medium to high boiling points, such as kerosine or diesel fuel, furthermore coal-tar oils and oils of plant or animal origin, aliphatic, cyclic and aromatic hydrocarbons, for example benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene, isophorone, strongly polar solvents, for example dimethylformamide, dimethyl sulfoxide, N-methylpyrrolidone, and water.

Aqueous use forms can be prepared from emulsion concentrates, pastes or wettable powders (spray powders, oil dispersions) by addition of water. To prepare emulsions, pastes or oil dispersions, the substances can be homogenized in water as such or dissolved in an oil or solvent, by means of wetting agents, tackifiers, dispersants or emulsifiers. However, concentrates comprising active compound, wetting agent, tackifier, dispersant or emulsifier and possibly solvent or oil which are suitable for dilution with water can also be prepared.

Suitable surfactants are the alkali metal, alkaline earth metal and ammonium salts of lignosulfonic acid, naphthalenesulfonic acid, phenolsulfonic acid, and dibutylnaphthalenesulfonic acid, alkylarylsulfonates, alkyl sulfates, alkylsulfonates, fatty alcohol sulfates and fatty acids and alkali metal salts and alkaline earth metal salts thereof, salts of sulfated fatty alcohol glycol ethers, condensation products of sulfonated naphthalene and naphthalene derivatives with formaldehyde, condensation products of naphthalene or of naphthalene sulfonic acid with phenol and formaldehyde, polyoxyethylene octylphenol ethers, ethoxylated isooctylphenol, octylphenol and nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Powders, compositions for broadcasting and dusts can be prepared by mixing or joint grinding the active substances with a solid carrier.

The formulations generally comprise from 0.01 to 95% by weight, preferably from 0.1 to 90% by weight, of the active compound. The active compounds are employed in a purity of from 90% to 100%, preferably from 95% to 100% (according to the NMR spectrum).

EXAMPLES OF FORMULATIONS ARE:

I. 5 parts by weight of a compound according to the invention are thoroughly mixed with 95 parts by weight of finely divided kaolin. This affords a dusting composition comprising 5% by weight of the active compound.

II. 30 parts by weight of a compound according to the invention are thoroughly mixed with a mixture of 92 parts by weight of pulverulent silica gel and 8 parts by weight of paraffin oil which had been sprayed onto the surface of this silica gel. This affords an active compound preparation having good adhesive properties (active compound content 23% by weight).

III. 10 parts by weight of a compound according to the invention are dissolved in a mixture comprising 90 parts by weight of xylene, 6 parts by weight of the addition product of 8 to 10 mol of ethylene oxide to 1 mol of oleic acid N-monoethanolamide, 2 parts by weight of the calcium salt of dodecylbenzenesulfonic acid and 2 parts by weight of the addition product of 40 mol of ethylene oxide to 1 mol of castor oil (active compound content 9% by weight).

IV. 20 parts by weight of a compound according to the invention are dissolved in a mixture comprising 60 parts by weight of cyclohexanone, 30 parts by weight of isobutanol, 5 parts by weight of the addition product of 7 mol of ethylene oxide to 1 mol of isooctylphenol and 5 parts by weight of the addition product of 40 mol of ethylene oxide to 1 mol of castor oil (active compound content 16% by weight).

V. 80 parts by weight of a compound according to the invention are mixed well with 3 parts by weight of the sodium salt of diisobutylnaphthalene-α-sulfonic acid, 10 parts by weight of the sodium salt of a lignosulfonic acid from a sulfite waste liquor and 7 parts by weight of pulverulent silica gel, and ground in a hammer mill (active compound content 80% by weight).

VI. 90 parts by weight of a compound according to the invention are mixed with 10 parts by weight of N-methyl-α-pyrrolidone, affording a solution which is suitable for use in the form of very small drops (active compound content 90% by weight).

VII. 20 parts by weight of a compound according to the invention are dissolved in a mixture comprising 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. The solution is poured into 100,000 parts by weight of water and finely dispersed therein, affording an aqueous dispersion comprising 0.02% by weight of active compound.

VIII. 20 parts by weight of a compound according to the invention are mixed well with 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel, and ground in a hammer mill. The mixture is finely dispersed in 20,000 parts by weight of water, affording a spray liquor comprising 0.1% by weight of active compound.

Granules, for example coated granules, impregnated granules and homogeneous granules, can be prepared by binding the active compounds to solid carriers. Solid carriers are, for example, mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and products of vegetable origin, such as cereal meal, tree bark meal, wood meal and nutshell meal, cellulose powders and other solid carriers.

Oils of various types, herbicides, fungicides, other pesticides and bactericides can be added to the active compounds, if desired even immediately prior to application (tank mix). These agents can be added to the compositions according to the invention in a weight ratio of 1:10 to 10:1.

SYNTHESIS EXAMPLES

Example 1

1-Cyano-N-[(1R)-1-napht-2-yl-ethyl]-2,2,3,3-tetramethylcyclopropanecarboxamide a) Methyl 2-Cyano-3-methylbut-2-enoate 87 g (1.5 mol) of acetone were initially charged in 100 ml of benzene. After addition of 131 g (1.33 mol) of methyl cyanoacetate, 16 g (0.28 mol) of acetic acid and 9.7 g (0.13 mol) of ammonium acetate, the mixture was heated at reflux on a water separator for 10 hours. For work-up, the mixture was washed twice with ¼-concentrated hydrochloric acid and water. The solution was dried with magnesium sulfate and the solvent was removed, and the resulting crude product was distilled. 108 g (55% yield) of methyl 2-cyano-3-methyl-but-2-enoate were isolated (B.p. 95° C./5.2 mbar).

b) Methyl 1-Cyano-2,2,3,3-tetramethylcyclopropane-1-carboxylate

The title compound was synthesized similarly to J. Org. Chem. 50 (1985), 2807–2809: 5.6 g (50mmol) of potassium tert-butoxide were initially charged in 15 ml of dimethyl sulfoxide, and 4.4 g (50 mmol) of nitropropane dissolved in 190 ml of dimethyl sulfoxide were slowly added dropwise. After addition of 5 g (36 mmol) of methyl 2-cyano-3-methylbut-2-enoate dissolved in 10 ml of dimethyl sulfoxide, the mixture was stirred at room temperature for 40 hours. The reaction was quenched by slow addition of water. The reaction mixture was extracted three times with methyl tert-butyl ether. The organic phases were dried with magnesium sulfate and freed from ether giving the crude product (9 g), which was employed for the next reaction without any further purification.

c) 1-Cyano-2,2,3,3-tetramethylcyclopropane-1-carboxylic acid

The crude methyl 1-cyano-2,2,3,3-tetramethylcyclopropyl-1-carboxylate (9 g) was hydrolyzed by refluxing for 4 hours in a mixture of identical parts of methanol, tetrahydrofuran and 2 N aqueous sodium hydroxide solution (70 ml each). For work-up, the same volume of 2 N aqueous sodium hydroxide solution was added and the mixture was extracted repeatedly with ether. The aqueous phase was acidified with hydrochloric acid and the 1-cyano-2,2,3,3-tetramethylcyclopropyl-1-carboxylic acid was then isolated as a white solid by extraction with methylene chloride, drying with magnesium sulfate and removal of the solvent (5.5 g; 66% yield over 2 steps).

d) 1-Cyano-N-[(1R)-1-naphth-2-yl-ethyl]-2,2,3,3-tetramethylcyclopropanecarboxamide 0.61 g (6 mmol) of triethylamine was added to a solution of 1.0 g (6 mmol) of 1-cyano-2,2,3,3-tetramethylcyclopropane-1-carboxylic acid (cf. Org. Prep. Proced. Int. 5, (1973), 25–29) and 1.03 g (6 mmol) of (1 R)-1-naphth-2-ylethylamine in 50 ml of dichloromethane. At 10° C., 0.94 g of 93% pure diethyl cyanophosphonate (6 mmol) was then added dropwise, and the mixture was stirred at room temperature for 12 hours. The reaction solution was concentrated using a rotary evaporator and then purified by silica gel chromatography (mobile phase: methyl tert-butyl ether:hexane=1:9, then 3:7). 1.9 g (99% yield) of the title compound were isolated as a white solid of melting point 169–1750° C.

Example 2

(1R,3S/1S,3R)-2,2-Dichloro-N-[(1R)-1-naphth-2-ylethyl]-1-ethyl-3-methylcyclopropanecarboxamide a) Ethyl 2,2-Dichloro-1-ethyl-3-methylcyclopropane-1-carboxylate 38 g (0.27 mol) of ethyl 2-ethylbut-2-enoate, 2.2 g (0.01 mol) of benzyltriethylammonium chloride and 57 ml of 50% strength aqueous sodium hydroxide solution were initially charged in 180 ml of dichloromethane. At 35° C. –40° C., 95 ml of chloroform were added dropwise over a period of 1 hour. After a reaction time of 5 hours at 40° C., the mixture was stirred at room temperature for a further 14 hours. For work-up, the reaction solution was poured into 1.5 l of water. The organic phase was removed and the aqueous phase was then extracted with dichloromethane. The combined organic phases were washed with water and, after drying with magnesium sulfate, concentrated. The residue (47 g) was subjected to vacuum distillation. The title compound was isolated as a colorless liquid (25.7 g, 43% yield, boiling point 71° C. at 2 mbar).

b) 2,2-Dichloro-1-ethyl-3-methylcyclopropane-1-carboxylic Acid

The ester was hydrolyzed similarly to Example 1d). The product was isolated as a yellowish-white resin (19.7 g; 91% yield).

c) 2,2-Dichloro-1-ethyl-3-methylcyclopropane-1-carbonyl Chloride

To generate the acyl chloride, 19.7 g (0.1 mol) of 2,2-dichloro-1-ethyl-3-methylcyclopropane-1-carboxylic acid were dissolved in toluene, and 36.9 g (0.31 mol) of thionyl chloride were added. After a reaction time of 5 hours at reflux, the mixture was stirred at room temperature for a further 14 hours. The reaction solution was concentrated using water pump vacuum. 22 g of a brown liquid were isolated as crude product. This was not purified prior to further use.

d) (1R,3S/1S,3R)-2,2-dichloro-N[(1R)-1-naphth-2-yl-ethyl]-1-ethyl-3-methylcyclopropanecarboxamide 0.62 g (2.9 mmol) of 2,2-dichloro-1-ethyl-3-methylcyclopropane-1-carbonyl chloride was initially charged in 20 ml of abs. dichloromethane. 0.5 g (2.9 mmol) of (1R)-1-naphth-2-yl-ethylamine and 0.3 g (2.9 mmol) of triethylamine were added, and the mixture was then stirred at room temperature for 16 hours. For work-up, the reaction solution was diluted with the same volume of dichloromethane and washed with 2N hydrochloric acid, 2 N aqueous sodium hydroxide solution and water. The organic phase was dried with magnesium sulfate and the solvent was removed, after which the title compound was isolated as a solid (0.9 g; 81% yield). The mixture of diastereomers had a melting point of 120–135° C.

Example 3

(1S,3R/1R,3S)-2,2-Dichloro-1-ethyl-3-methylcyclopropanecarboxylic Acid [(1R/1S)-1-Methyl-1-naphth-2-yl-propyl]amide Similarly to Example 1d), but with twice the amount of triethylamine, 0.94 g (4 mmol) of 2,2-dichloro-1-ethyl-3-methylcyclopropane-1-carbonyl chloride was reacted with 0.86 g (4 mmol) of 1-methyl-1-naphth-2-ylpropylamine hydrochloride to give the title compound. After purification by silica gel column chromatography (mobile phase: cyclohexane/ethyl acetate gradient), the resinous product was isolated as a mixture of diastereomers (1.1 g; 73% yield).

Physical data (NMR in $CDCl_3$, stated in ppm)=$^1$H-NMR: 0.8; 1.1; 1.2; 1.3; 1.6; 1.9; 2.2.

Example 4

(1S,3R/1R,3S)-2,2-Dichloro-1-ethyl-3-methylcyclopropanecarboxylic Acid [(1R/1S)-1-Methyl-1-naphth-1-ylpropyl]amide Similarly to Example 1d), 0.25 g (1.1 mmol) of 2,2-dichloro-1-ethyl-3-methylcyclopropane-1-carbonyl chloride was reacted with 0.23 g (1.1 mmol) of 1-methyl-1-naphth-1-ylpropylamine hydrochloride. The title compound was isolated, after purification by silica gel column chromatography (mobile phase: cyclohexane/ethyl acetate gradient), as a resinous mixture of diastereomers (0.15 g; 38% yield).
$^1$H-NMR: 0.8; 1.1–1.3; 1.6; 2.0; 2.5–2.6; 6.2; 7.4; 7.6; 7.8–8.0; 8.6.

Example 5

1-Methylcyclopropanecarboxylic Acid [(1R)-1-Naphth-2-yl-ethyl]-amide

Similarly to Example 1d), 1.5 g (15 mmol) of 1-methylcyclopropane-1-carboxylic acid were reacted with 2.6 g (15 mmol) of (1R)-1-naphth-2-ylethylamine to give the title compound. The product was isolated, after purification by silica gel chromatography (mobile phase: cyclohexane/ethyl acetate gradient), as a white solid (2.9 g; 76% yield, melting point 91° C.).

Example 6

1-Cyano-2,2,3-trimethylcyclopropanecarboxylic Acid [(1R)-1-Naphth-2-ylethyl]amide a) Methyl 2-Cyanobut-2-enoate Similarly to Example 1a), acetaldehyde was reacted with methyl-cyanoacetate in a Knoevenagel reaction to give methyl 2-cyanobut-2-enoate.

b) Methyl 1-Cyano-2,2,3-trimethylcyclopropane-1-carboxylate

Similarly to Example 1b), methyl 2-cyano-but-2-enoate was reacted to give methyl 1-cyano-2,2,3-trimethylcyclopropane-1-carboxylate.

c) 1-Cyano-2,2,3-trimethylcyclopropane-1-carboxylic Acid

Similarly to Example 1c), methyl 1-cyano-2,2,3-trimethylcyclopropane-1-carboxylate was hydrolyzed to give 1-cyano-2,2,3-trimethylcyclopropane-1-carboxylic acid.

d) 1-Cyano-2,2,3-trimethylcyclopropanecarboxylic Acid [(1R)-1-Naphth-2-ylethyl]amide Similarly to Example 1d), the amide of 1-cyano-2,2,3-trimethylcyclopropane-1-carboxylic acid and (1R)-1-naphth-2-ylethylamine was formed. The title compound was isolated as a yellow resin.

$^1$H-NMR: 1.2–1.3; 1.4; 1.6; 2.1; 5.3; 6.5; 7.4; 7.8

Example 7

Isopropyl [1-(1R)-1-Naphth-2-ylethylcarbamoyl) cyclopropyl]-carbamate a) 1-Isopropoxycarbonylaminocyclopropanecarboxylic Acid 0.2 g (1.98 mmol) of 1-aminocyclopropane-1-carboxylic acid were initially charged in 10 ml of 12% strength aqueous sodium hydroxide solution. After addition of 0.24 g (1.98 mmol) of isopropyl chloroformate, the pH was adjusted to 9 by dropwise addition of 12% strength aqueous sodium hydroxide solution. The mixture was stirred at room temperature for 14 hours and then, for work-up, extracted twice with methyl tert-butyl ether. The pH was subsequently adjusted to 1–2 using phosphoric acid. The mixture was extracted three times using dichloromethane, the extracts were dried with magnesium sulfate and the solvent was removed, after which the title compound was isolated as a white solid (0.2 g; 54% yield).

b) Isopropyl [1-(1R)-1-Naphth-2-ylethylcarbamoyl)-cyclopropyl]-carbamate

To prepare the amide, 0.1 g (0.53 mmol) of 1-isopropoxycarbonylaminocyclopropanecarboxylic acid was initially charged in 30 ml of dichloromethane. After cooling to 10° C., 0.5 g (0.53 mmol) of triethylamine and 0.57 g (0.53 mmol) of ethyl chloroformate were added. After 2 hours of stirring, a further 0.5 g (0.53 mmol) of triethylamine and 0.9 g (0.53 mmol) of (1R)-1-naphth-2-ylethylamine were added dropwise. The mixture was stirred at room temperature for 16 hours and then, for work-up, washed once with 5% strength aqueous sodium hydroxide solution, twice with 2N hydrochloric acid and once with water. The organic phase was dried using magnesium sulfate, the solvent was removed and the residue was then purified by silica gel column chromatography (mobile phase: cyclohexane: methyl tert-butyl ether=9:1, 6:4, 1:1). The title compound was isolated as a white-yellowish resin (0.14 g; 75% yield).

$^1$H-NMR: 0.8–1.0; 1.2; 1.4; 1.6; 4.9–5.1; 5.3; 6.8; 7.5; 7.8.

Example 8

3-(2,2-Dichlorovinyl)-2,2-dimethylcyclopropanecarboxylic Acid (1R)-1-Napht-2-ylethylamide The starting material was obtained in accordance with J. Org. Chem. 53 (16) (1988), 3843–3845. 0.47 g (2.24 mmol) of 3-(2,2-dichlorovinyl)-2,2-dimethylcyclopropanoic acid was dissolved in 50 ml of abs. methylene chloride and mixed with 0.22 g (2.24 mmol) of triethylamine and 0.38 g (2.24 mmol) of (1R)-1-naphth-2-ylethylamine. The reaction flask was cooled to 0° C. and 0.33 g (2.02 mmol) of 93% pure ethyl cyanoacetate was then added.

After the addition had ended, the ice-bath was removed and the mixture was stirred overnight. For work-up, the reaction solution was washed successively with 2N aqueous sodium hydroxide solution, water, 2N hydrochloric acid, water, 2N aqueous sodium hydroxide solution and finally once more with water. The organic phase was dried with magnesium sulfate, the solvent was removed and the product was then isolated by silica gel column chromatography (mobile phase: cyclohexane/ethyl acetate 9.5:0.5; then 7:3), as a yellow resin. Since a diastereomeric starting material was employed, the title compound 3-(2,2-dichlorovinyl)-2, 2-dimethylcyclopropanecarboxylic acid [(1R)-1-naphth-2-ylethyl]amide was likewise obtained as a mixture of diastereomers (0.5 g; 62% yield).

Physical data ($^1$H-NMR, CDCl$_3$, in ppm): 1.1–1.3; 1.4; 1.6; 1.9; 2.3; 5.3; 5.6; 5.8; 6.4; 7.4; 7.7–7.9.

Example 9

3-(2-Chloro-3,3,3-trifluoropropenyl)-2,2-dimethylcyclopropane-carboxylic Acid [(1R)-1-Naphth-2-yl-ethyl]amide, (E)-Isomer In accordance with the patent JP 62/116531, the starting material was obtained as a mixture of diastereomers.

0.54 g (2.24 mmol) of (E)-3-(2-chloro-3,3,3-trifluoropropenyl)-2,2-dimethylcyclopropanecarboxylic acid was dissolved in 50 ml of abs. methylene chloride and mixed with 0.22 g (2.24 mmol) of triethylamine and 0.38 g (2.24 mmol) of (1R)-1-napht-2-ylethylamine. The reaction flask was cooled to 0° C. and 0.33 g (2.02 mmol) of 93% pure ethyl cyanoacetate was then added.

After the addition had ended, the ice-bath was removed and the mixture was stirred overnight. For work-up, the reaction solution was washed with 2N aqueous sodium hydroxide solution, then with water, 2N hydrochloric acid, water, 2N aqueous sodium hydroxide solution and finally once more with water. The organic phase was dried with magnesium sulfate, the solvent was removed and the product was then isolated by separation by silica gel column chromatography (mobile phase: cyclohexane/ethyl acetate 9.5:0.5; then 7:3). This gave 0.7 g (79% yield) of the diastereomeric title compound as yellowish crystals (melting point 75° C.–77° C.).

Example 10

3-(2-Chloro-3,3,3-trifluoropropenyl)-2,2-dimethylcyclopropanecarboxylic Acid [(1R)-1-Naphth-2-yl-ethyl]amide, (Z)-Isomer In accordance with the patent JP 62/116531, the starting material was obtained as a mixture of diastereomers.

0.54 g (2.24 mmol) of (Z)-3-(2-chloro-3,3,3-trifluoropropenyl)-2,2-dimethylcyclopropanecarboxylic acid was dissolved in 50 ml of abs. methylene chloride and mixed with 0.22 g (2.24 mmol) of triethylamine and 0.38 g (2.24 mmol) of (1R)-1-napht-2-ylethylamine. The reaction flask was cooled to 0° C. and 0.33 g (2.02 mmol) of 93% pure ethyl cyanoacetate was then added.

After the addition had ended, the ice-bath was removed and the mixture was stirred overnight. For work-up, the reaction solution was washed with 2N aqueous sodium hydroxide solution, then with water, 2N hydrochloric acid, water, 2N aqueous sodium hydroxide solution and finally once more with water. The organic phase was dried with magnesium sulfate, the solvent was removed and the product was then isolated by purification by silica gel column chromatography (mobile phase: cyclohexane/ethyl acetate= 9.5:0.5; then 7:2). This gave 0.6 g (68% yield) of the diastereomeric title compound as yellow resin.

Physical data: ($^1$H, CDCl$_3$, in ppm): 1.2–1.3; 1.4; 1.5–1.6; 2.5; 5.3; 5.9; 6.1; 7.4; 7.7–7.9.

Example 11

USE EXAMPLES

The fungicidal activity of the compounds of the formula I against harmful fungi was demonstrated by the following greenhouse experiments:

The active ingredients were formulated as a 20% strength emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Emulphor® EL (Emulan® EL, emulsifier based on ethoxylated fatty alcohols) and diluted with water to give the desired concentration.

1. Activity Against *Pyricularia oryzae* (Protective)

Leaves of rice seedlings (cultivar "Tai-Nong 67") grown in pots were treated with the aqueous preparation of the active ingredients (comprising 250 ppm). After approximately 24 hours, the plants were inoculated with an aqueous spore suspension of *Pyricularia oryzae*. The plants which had been treated in this manner were placed for 6 days into controlled-environment cabinets at 22–24° C. and a relative atmospheric humidity of 95 to 99%. The extent of the disease which had developed on the leaves was subsequently determined visually.

In this test, the plants which had been treated with the compounds according to the invention showed a low disease level, while the disease level of the untreated plants was 80%.

2. Systemic Activity Against *Pyricularia oryzae*

Pregerminated rice (cultivar "Tai-Nong 67") was grown in a hydroponic system with Hoagland solution until it had reached the two-leaf stage. Then, the aqueous preparation of the active ingredients (comprising 50 ppm) was poured next to the roots. After the plants had grown in the greenhouse for another five days, they were inoculated with an aqueous spore suspension of *Pyricularia oryzae*. The plants which had been treated in this manner were placed for 6 days into controlled-environment cabinets at 22–24° C. and a relative atmospheric humidity of from 95 to 99%. The extent of the disease which had developed on the leaves was subsequently determined visually.

In this test, the plants which had been treated with the compounds according to the invention showed a low disease level, while the disease level of the untreated plants was 80%.

We claim:

1. A cycloalkylcarboxamide of the formula Ia

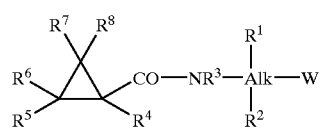

Ia where:

Alk is straight-chain or branched $C_1$–$C_6$-alkylene;

$R^1$ is $C_1$–$C_6$-alkyl or $C_2$–$C_6$-alkenyl, where these radicals may be partially or fully halogenated and/or may carry one or two of the following groups: $C_1$–$C_4$-alkoxy, $C_1$–$C_4$-haloalkoxy, $C_1$–$C_4$-alkylthio, $C_1$–$C_4$-alkoxycarbonyl, $C_3$–$C_6$-cycloalkyl and phenyl, where the phenyl may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_3$–$C_6$-cycloalkyl or heterocyclyl;

$R^2$, $R^3$ are hydrogen, $C_1$–$C_6$-alkyl or $C_2$–$C_6$-alkenyl, where these radicals may be partially or fully halogenated;

W is a fused bicyclic ring system having in each case six ring atoms, where one or two carbon ring atoms may be replaced by nitrogen atoms, and where these ring systems may carry one to three of the following groups: nitro, halogen, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_3$–$C_6$-cycloalkyl and $C_1$–$C_4$-alkoxycarbonyl;

$R^4$ is hydrogen, halogen, cyano, $C_1$–$C_6$-alkyl, $C_2$–$C_6$-alkenyl, $C_1$–$C_6$-alkoxy or $C_1$–$C_6$-alkylthio, where these radicals may be partially or fully halogenated and/or may carry one or two of the following groups: $C_1$–$C_4$-alkoxy, $C_1$–$C_4$-haloalkoxy, $C_1$–$C_4$-alkylthio, $C_1$–$C_4$-alkoxycarbonyl, $C_3$–$C_6$-cycloalkyl, $C_1$–$C_6$-alkoxycarbonylamino;

$R^5$ is hydrogen, halogen, cyano, $C_1$–$C_6$-alkyl, $C_2$–$C_6$-alkenyl, $C_1$–$C_6$-alkoxy or $C_1$–$C_6$-alkylthio, where these radicals may be partially or fully halogenated and/or may carry one or two of the following groups: $C_1$–$C_4$-alkoxy, $C_1$–$C_4$-haloalkoxy, $C_1$–$C_4$-alkylthio, $C_1$–$C_4$-alkoxycarbonyl, $C_3$–$C_6$-cycloalkyl, $C_1$–$C_4$-alkoxycarbonylamino;

$R^6$ is hydrogen, halogen or $C_1$–$C_6$-alkyl;

$R^7$ is hydrogen, halogen or $C_1$–$C_6$-alkyl;

$R^8$ is hydrogen, halogen or $C_1$–$C_6$-alkyl, and their agriculturally useful salts.

2. A cycloalkylcarboxamide of the formula Ia as claimed in claim 1, where the cyclopropyl ring may carry one to five substituents $R^4$–$R^8$ selected from the group of the radicals consisting of halogen, cyano and $C_1$–$C_3$-alkyl.

3. A cycloalkylcarboxamide as claimed in claim 1, where $R^4$ is halogen, cyano, $C_1$–$C_6$-alkyl, $C_1$–$C_4$-alkoxycarbonylamino, $C_1$–$C_4$-alkoxy or $C_1$–$C_4$-alkylthio.

4. A cycloalkylcarboxamide as claimed in in claim 1, where $R^5$ is hydrogen or $C_1$–$C_6$-alkyl.

5. A cycloalkylcarboxamide as claimed in claim 1, where $R^6$ is hydrogen or $C_1$–$C_6$-alkyl.

6. A cycloalkylcarboxamide as claimed in claim 1, where $R^7$ is hydrogen, chlorine or $C_1$–$C_6$-alkyl.

7. A cycloalkylcarboxamide as claimed in claim 1, where $R^8$ is hydrogen, chlorine or $C_1$–$C_6$-alkyl.

8. A cycloalkylcarboxamide as claimed in claim 1, where $R^1$ is $C_1$–$C_6$-alkyl and $R^2$ is hydrogen or $C_1$–$C_6$-alkyl.

9. A cycloalkylcarboxamide as claimed in claim 1, where Alk is a methylene group.

10. A composition comprising a fungicidally effective amount of at least one cycloalkylcarboxamide of the formula I as claimed in claim 1 and, if appropriate, an inert liquid and/or solid carrier and, if appropriate, at least one surfactant.

11. A method for controlling harmful fungi, which comprises treating the harmful fungi, their habitat or the plants, areas, materials or spaces to be kept free from them with an effective amount of a cycloalkylalkanecarboxamide of the formula I as claimed in claim 1.

* * * * *

UNITED STATES PATENT AND TRADEMARK OFFICE
CERTIFICATE OF CORRECTION

PATENT NO.    : 6,441,044 B1
DATED         : August 27, 2002
INVENTOR(S)   : Rose et al.

It is certified that error appears in the above-identified patent and that said Letters Patent is hereby corrected as shown below:

Column 20,
Line 65, "and their" should be -- or an --; "salts" should be -- salt thereof --.
Line 66, delete "A" and replace with -- The --
Line 66, delete "claimed" and substitute -- defined --

Column 21,
Line 1, delete "of the radicals".
Lines 1, 3, 6, 8, 10 and 12, delete "A" and replace with -- The --
Lines 1, 3, 6, 8, 10 and 12, delete "claimed" and substitute -- defined --

Column 22,
Lines 4 and 5, "of the formula I as claimed" should be -- formula Ia defined --.
Line 10, "or the plants" should be -- or plants --.
Line 11, "them" should be -- the fungi --.
Lines 12 and 13, "a cycloalkylalkanecarboxamide of the formula I as claimed" should be -- the cycloalkylcarboxamide of formula Ia defined --.

Signed and Sealed this

Twenty-eighth Day of January, 2003

JAMES E. ROGAN
*Director of the United States Patent and Trademark Office*